United States Patent
Vettorazzo

(10) Patent No.: US 9,283,107 B2
(45) Date of Patent: Mar. 15, 2016

(54) PUMP FOR PRODUCING OR IMPROVING HUMAN PENIS ERECTION

(75) Inventor: Dario Vettorazzo, Caldogno (IT)

(73) Assignee: Cinzia Romana Ribau, Caldogno (VI) (IT)

( * ) Notice: Subject to any disclaimer, the term of this patent is extended or adjusted under 35 U.S.C. 154(b) by 0 days.

(21) Appl. No.: 14/401,873

(22) PCT Filed: May 31, 2012

(86) PCT No.: PCT/IB2012/052729
§ 371 (c)(1),
(2), (4) Date: May 1, 2015

(87) PCT Pub. No.: WO2013/175273
PCT Pub. Date: Nov. 28, 2013

(65) Prior Publication Data
US 2015/0305915 A1    Oct. 29, 2015

(30) Foreign Application Priority Data

May 23, 2012  (IT) .............................. PD2012A0163

(51) Int. Cl.
*A61F 5/41*    (2006.01)

(52) U.S. Cl.
CPC ............. *A61F 5/41* (2013.01); *A61F 2005/412* (2013.01)

(58) Field of Classification Search
CPC   A61F 5/41; A61F 2005/412; A61F 2005/415
USPC ...................................... 600/38–41
See application file for complete search history.

(56) References Cited

U.S. PATENT DOCUMENTS 9,039,598 B2 * 5/2015 Narin ........................ A61F 5/41
                                                           600/38
2005/0033113 A1    2/2005 Bonthuys

FOREIGN PATENT DOCUMENTS

| GB | 2417686 | 3/2006 |
|---|---|---|
| WO | 2010094677 | 8/2010 |
| WO | 2011135374 | 11/2011 |

* cited by examiner

*Primary Examiner* — John Lacyk
(74) *Attorney, Agent, or Firm* — Themis Law

(57) ABSTRACT

A pump to produce or improve human penis erection includes a substantially tubular inner assembly having a rimmed annular edge suited to accommodate an erect human penis, a translating assembly sliding along the inner assembly having an end shaped like a dome with an opening or circular seat suited to accommodate a valve and a lid, a bellows having two annular edges suited to be connected and joined respectively with the rimmed annular edge of the inner assembly, where the valve has a first substantially disk-shaped part, the center of which has a second substantially linear part perpendicular to the disk-shaped part, and where the lid includes a circular element having an elongated hole or slot in a radial direction, through which the second linear part of the valve is housed and protrudes, as well as one or more additional through holes.

9 Claims, 3 Drawing Sheets

PUMP FOR PRODUCING OR IMPROVING HUMAN PENIS ERECTION

FIELD OF THE INVENTION

This patent relates to pumps to produce or improve human penis erection and in particular relates to a new water-based pump to produce or improve human penis erection.

BACKGROUND OF THE INVENTION

Penis erection pumps for humans are already known. They consist of a chamber to be applied on the penis so that it adheres to the skin at the base of the penis.

The air is extracted from this chamber by creating a vacuum inside the chamber itself. This vacuum causes increased blood flow to the penis producing an erection of the penis.

Some known pumps include a manual bulb-type pump, connected with the chamber through a tube or conduit and a valve. Acting on the manual pump results in the extraction of the air from the chamber obtaining the desired vacuum within the chamber and the erection of the penis positioned in the chamber.

Other types of pumps comprise a bell-shaped tubular element the circular open end of which is joined to a bellows-type tubular element.

The penis is positioned inside the bellows and the bell-shaped tubular element so that the open annular edge of the bellows rests against the body at the base of the penis.

A non-return valve is contained and housed in a cap screwed onto the dome of the bell-shaped tabular element while on the body of the bell-shaped tubular element there is a decompression valve.

Water is inserted inside the bell-shaped tubular element and the bellows which are applied on the penis and adhere to the groin around the penis by means of the cap so as to fill the pump. The cap is then closed.

Translating the tubular bell-shaped element with an alternating motion the water is expelled from the chamber comprised of the bell-shaped tubular element and the bellows creating a vacuum that causes and promotes the flow of blood to the penis.

The pumps of the known art for producing or improving human penis erection comprise two valves or two non-return valve systems, of which one or more valves operate automatically suited to allow only the extraction of water from the inner chamber, and one or more manually operated valves suited to allow the ingress of air into the inner chamber.

The valves only used for the extraction of water from the inner chamber facilitate the production of a vacuum inside the chamber during the normal use of the pump.

The valves to allow the ingress of air in the inner chamber during the operation of the pump maintain the vacuum in the inner chamber and, when they are manually operated at the end of the use of the pump, they allow the air to enter the inner chamber enabling the pump to be removed from the user's body.

SUMMARY OF THE INVENTION

The object of the present patent is a new water pump to produce or improve human penis erection.

One object of the new pump is to use a single valve both to maintain the vacuum in the inner chamber and to restore the atmospheric pressure in the inner chamber itself.

Another object of the new pump is to allow a simple actuation of the valve to restore the atmospheric pressure in the inner chamber.

A further object of the new pump is to separate the penis of the user from moving parts of the pump.

Yet another object of the new pump is to have a small number of simple parts.

A further object of the new pump is to use water as the decompression fluid in contact with the penis.

These and other aims, direct and complementary, are achieved by the new water pump to produce or improve human penis erection comprising an internal tubular housing element, an external bell-shaped tubular element suited to slide externally over the housing tubular element, an elastic element for the sealed connection between the tubular housing and the bell-shaped tubular element, a movable elastic adjustment element for the internal pressure, a holding element of the movable elastic element, a seal gasket to rest the assembly against the body in the groin area around the penis.

The tubular housing element, hereafter referred to as the inner assembly, is comprised of a rigid cylinder having a widened annular edge at one end. The inner assembly has an internal diameter and length suitable to accommodate an erect human penis.

The outer surface of the inner assembly foresees raised reliefs or ribs, arranged parallel to the length of the inner assembly itself.

The tubular bell-shaped element, herein after referred to as the translating assembly, is comprised of a rigid tubular element with a dome-shaped end. The translating assembly has a length and an internal diameter such as to slide externally on the inner assembly and on the external ribs or raised reliefs of the inner assembly.

The dome-shaped end has an opening or circular seat suited to receive the movable elastic element and the relative holding element.

The end of the translating assembly, opposite to the dome-shaped end, is connected to the end with the rimmed annular edge of the inner assembly through an air-tight elastic connection element.

Both the inner assembly and translating assembly are preferably made of transparent material.

The translating assembly has a graduated scale.

The air-tight elastic connection element, hereinafter referred to as the bellows, is comprised of a corrugated flexible sleeve having the two annular edges suited to be connected and joined respectively with the rimmed annular edge of the inner assembly and with the end opposite to the dome-shaped end of the translating assembly.

The wall of the bellows has a longitudinal section comprised of portions at opposed inclinations so as to allow its elongation or shortening.

The movable elastic element to adjust the internal pressure, hereinafter referred to as valve, is comprised of an element of plastic material comprised of a first substantially disk-shaped part with four radial reliefs on the circumference, at the center of which there is a second substantially linear part with a circular cross-section perpendicular to the disk-shaped part. A third wall-shaped part generally rectangular is joined to the first disc-shaped part on the same side as the second linear part in the space between the edge of the first disc-shaped part and the second linear part. In particular, the third wall-shaped part is generally passing through the line of the first disk-shaped part passing through the joint edge of the third wall-shaped part with the first disc-shaped part.

The design foresees that the third wall-shaped part is tilted with respect to the first disk-shaped part in the direction opposite to the second linear part. The valve is suited to be housed in the hole or round seat of the dome-shaped end of the translating assembly.

The design also foresees a gasket of elastic material on the side of the first disk-shaped part of the valve opposite to the second and third part.

The holding element of the valve, hereinafter referred to as lid, is comprised of an element suited to be housed at least on the outer edge of the hole or seat of the dome-shaped end of the translating assembly.

In particular the lid is suited to be positioned and fixed, for example by pressure, in the hole or seat of the translating assembly.

The lid has at least one elongated hole or slot in the radial direction through which the second linear part of the valve is housed.

On the side of the lid facing the inner side of the translating assembly there is a seat or compartment to house the third wall-shaped part of the valve. The design foresees that the lid has one or more additional through-holes suitable to put the seat or compartment of the translating assembly and the environment in communication.

The edge or wall of the lid facing the translating assembly has recesses or seats to facilitate the application and removal of the lid from the translating assembly.

An elastic annular gasket is placed on the edge of the bellows corresponding to the rimmed annular edge of the inner assembly.

This gasket is suited to ensure the seal of the new pump on the groin around the user's penis.

The design foresees that the gasket and the bellows have the central hole facing the user's groin eccentric with respect to its outer circumference.

The characteristics of the new water pump to produce or improve human penis erection will be better clarified by the following description with reference to the drawings, annexed by way of non-limiting example.

DETAILED DESCRIPTION OF EMBODIMENTS OF THE INVENTION

Figure 1:
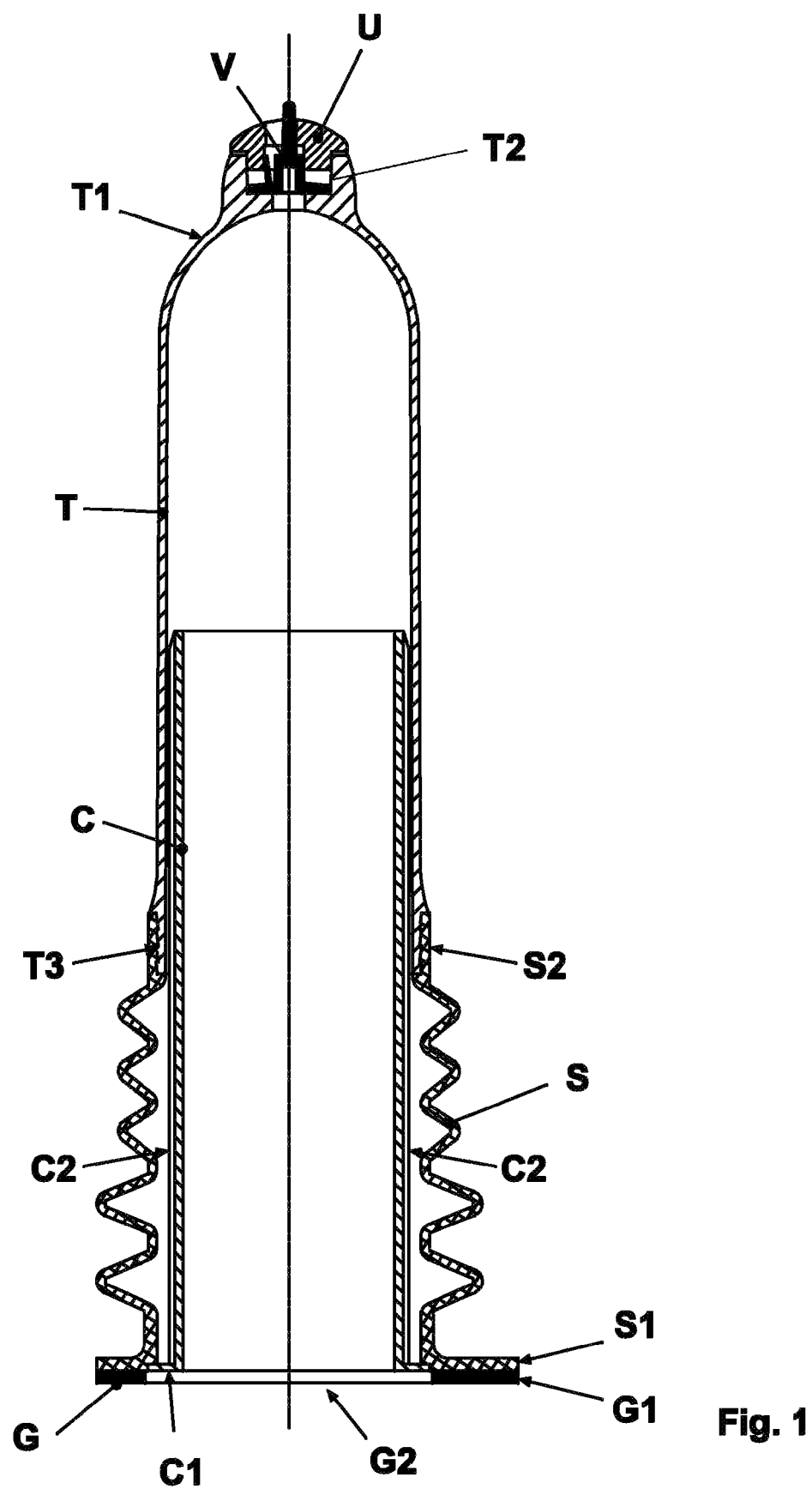
FIG. 1 shows a vertical section of a pump according to the invention.

With reference to FIG. 1, a pump according to the invention comprises an inner assembly (C), a translating assembly (T) sliding on the inner assembly (C), a bellows (S) for the sealed connection between the inner assembly (C) and the translating assembly (T), a valve (V), a lid (U), and an annular gasket (G).

The inner assembly (C) is comprised of a rigid cylinder having a rimmed annular edge (CI). This inner assembly (C) has an appropriate internal diameter and length to accommodate an erect human penis.

On the outer surface of the inner assembly (C) there are raised reliefs or ribs (C2) arranged parallel to the length of the inner assembly (C) itself.

The translating assembly (T) is comprised of a rigid tubular element having one dome-shaped end (T1).

Said translating assembly (T) has a length and internal diameter such as to slide externally along the inner assembly (C).

Figure 3:
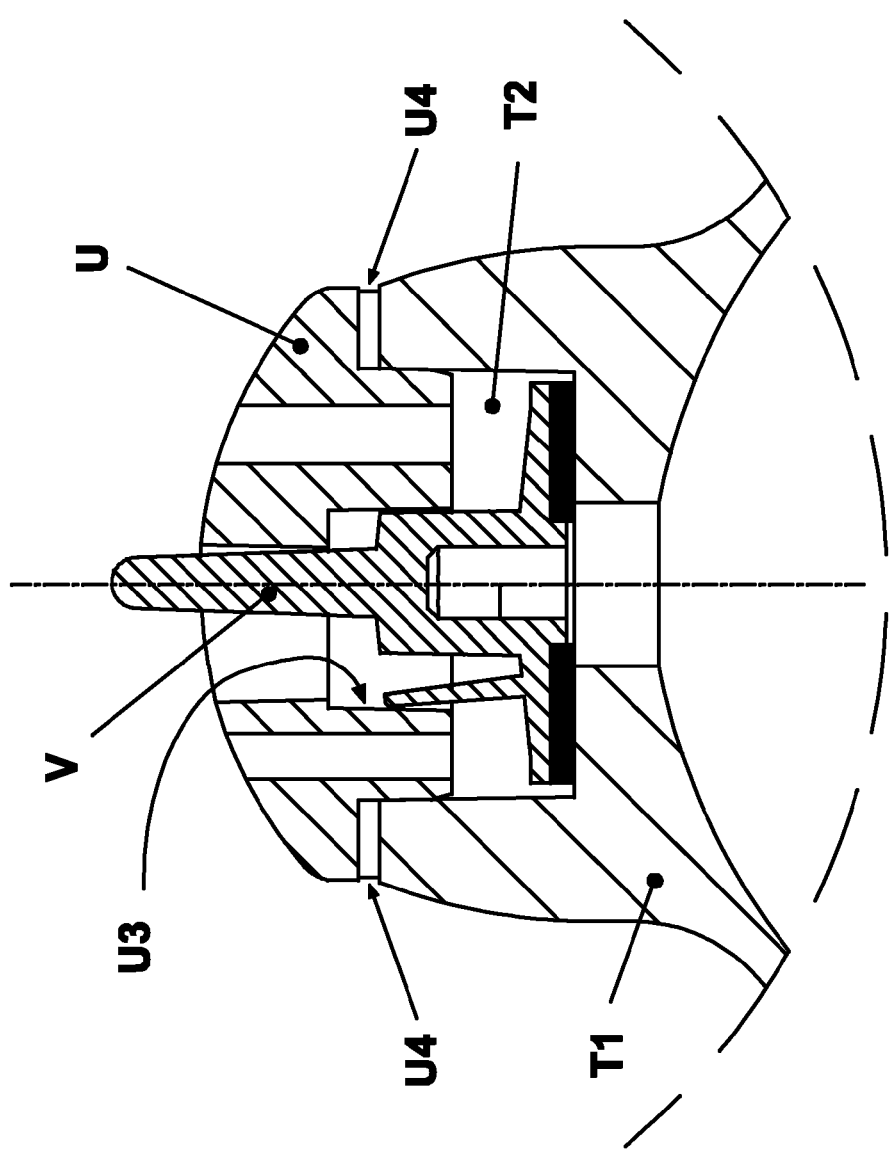
FIG. 3 shows a position of the valve of FIG. 2.

The dome-shaped end (T1) has an opening or round seat (T2) suited to house the valve (V) and the lid (U), as shown in FIG. 3.

The end (T3) of said translating assembly (T), opposite to the dome-shaped end (T1), is connected to the end with a rimmed annular edge (C1) of the inner assembly (C) through said bellows (S).

Said bellows (S) is comprised of a corrugated flexible sleeve having the two annular edges (S1, S2) suited to be connected and joined respectively with the rimmed annular edge (C1) of the inner assembly (C) and with the end (T3) opposite the dome-shape end (T) of said translating assembly (T).

Figure 2:
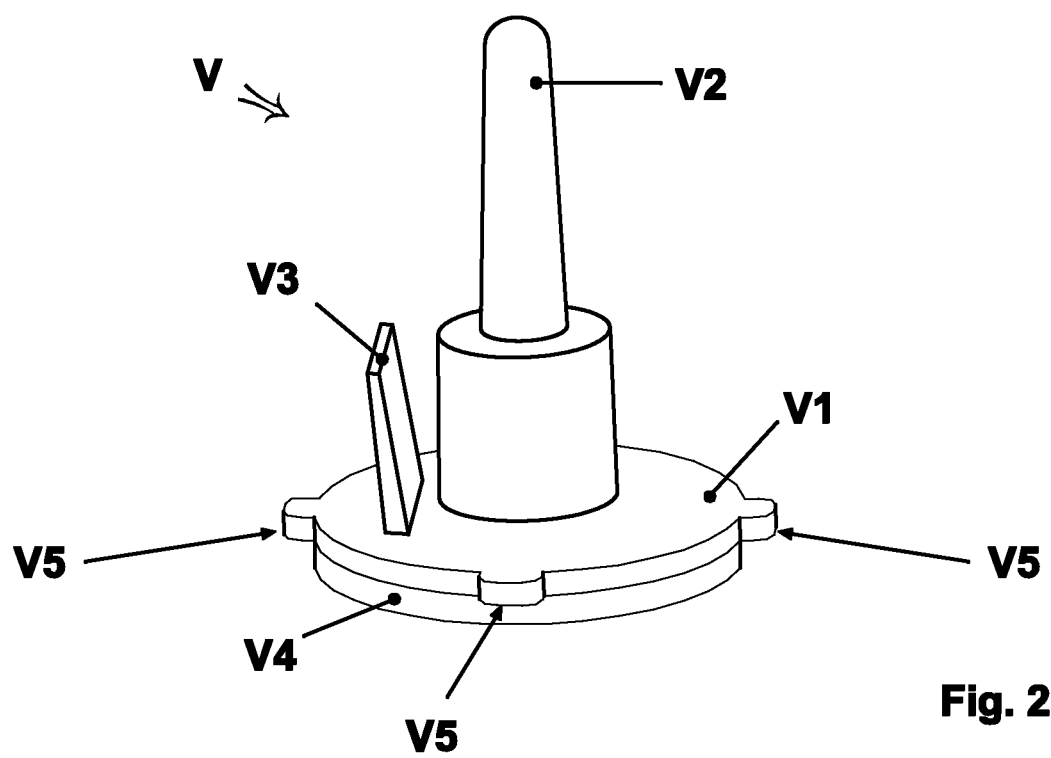
FIG. 2 shows a perspective view of a valve in a pump according to the invention.

The wall of said bellows (S) has its longitudinal section comprised of portions at opposed inclinations so as to allow its elongation or shortening. The valve (V), shown in isometric view in FIG. 2, is comprised of an element of plastic material comprised of a first substantially disk-shaped part (VI), having radial reliefs (V5) on the circumference, at the center of which there is a second substantially linear part (V2) with a circular cross-section perpendicular to the disk-shaped part (V1). A third generally rectangular wall-shaped part (V3) is joined to the first disc-shaped part (V1) on the same side as the second linear part (V2) in the space between the edge of the first disc-shaped part (V1) and the second linear part (V2).

On the side of said first disc-shaped part (V1) of the valve (V) opposite to said second part (V2) and third part (V3) there is a gasket (V4) made of elastic material.

Said valve (V) is suited to be seated in the hole or circular seat (T2) of the dome-shaped end (T1) of the translating assembly (T), as shown in the section of FIG. 3.

Figure 4:
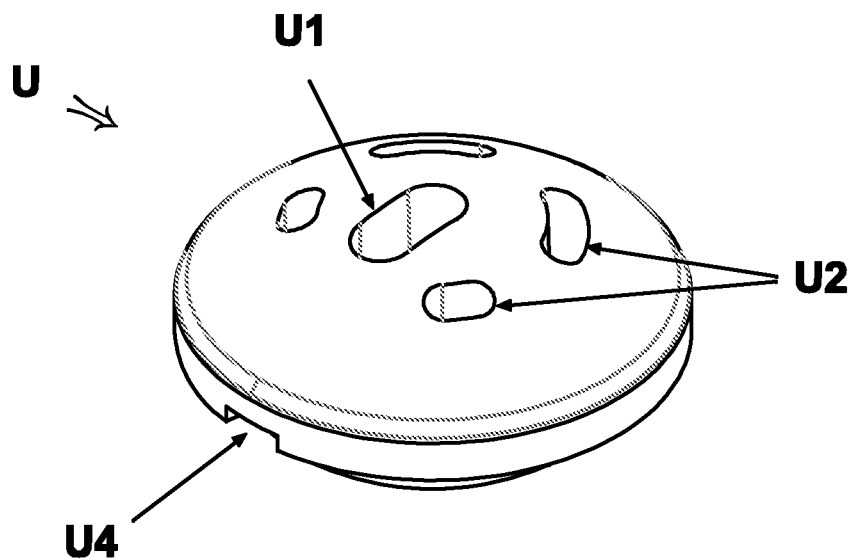
FIG. 4 shows a lid of a pump according to the invention.

The lid (U) shown in detail in FIG. 4, is comprised of an element suited to be housed at least on the outer edge of the hole or seat (T2) of the dome-shaped end (T1) of the translating assembly (T).

In particular, said lid (U) is suited to be positioned and fixed in the hole or seat (T2) of the translating assembly (T) by applying some pressure.

The lid (U) has an elongated hole or slot (U1) in a radial direction through which the second linear part (V2) of the valve (V) is housed and one or more additional through holes (U2) suited to put the seat or compartment (T2) of the translating assembly (T) in communication with the environment.

On the side of the lid (U) facing the inside of the translating assembly (T) there is a seat or compartment (U3) to house the third wall-shaped part (V3) of the valve (V).

The edge of the side of the lid (U) facing the inside of the translating assembly (T) has recesses or seats (U4) suited to facilitate the application and removal of said lid (U) from said translating assembly (T).

The air-tight annular gasket (G) is comprised of an element made of flexible material to be applied to the edge (S1) of the bellows (S) corresponding to the rimmed annular edge (CI) of the inner assembly (C).

In particular, the central hole (G2) of said annular gasket (G), and the corresponding hole of the bellows (S), are eccentric with respect to the circumferences of their outer edges (G1, S1).

The following describes the use of the new pump.

The new pump is entirely filled with water.

The flaccid or semi-erect penis is positioned inside the inner assembly (C) through the opening at the rimmed annular edge (C1) so that the annular gasket (G) rests on the user's pubic areal The user translates the sliding body (T) towards his body and away from his body thereby causing the compression of the water inside the inner assembly (C) and the translating assembly (T).

This compressed water pushes against the valve (V), opening it, and comes out of the new pump.

Translating the translating assembly (T) once again away from the body, creates a vacuum inside the new pump that promotes the flow of blood into the user's penis. This translation does not cause the return of air into the new pump as the valve (V) keeps the hole in the dome-shaped end (T1) of the translating assembly (T) closed.

Repeating the translation of the sliding assembly (T) several times, both away and towards the user's body, further water still inside the pump is expelled increasing the vacuum inside the new pump.

To remove the new pump from the user's body act on the end of the second linear part (V2) of the valve protruding from the hole or slot (U1) of the lid (U) so as to bend or lift the first annular part (V1) of the valve (V) itself and allow the air to flow inside the new pump restoring the ambient pressure within the new pump and discharging the water.

Therefore, with reference to the preceding description and the attached drawings, the following claims are made.

The invention claimed is:

1. A pump to produce or improve human penis erection comprising:
   a substantially tubular inner assembly (C) having a rimmed annular edge (C1) configured to accommodate an erect human penis;
   a translating assembly (T) configured to slide on said inner assembly (C) and having a dome-shaped opposite end to said rimmed annular edge (C1) of said inner assembly (C) with an aperture or circular seat (T2) suited to accommodate a valve (V) made of an elastic material and a lid (U); and
   a bellows (S) comprised of a sleeve made of a flexible material having two annular edges (S1, S2) configured to be connected and joined respectively with the rimmed annular edge (C1) of the inner assembly (C) and with an opposite end (T3) to the dome-shaped end (T1) of said translating assembly (T),
   wherein said valve (V) is comprised of a first substantially disk-shaped part (V1), a center of which has a second substantially linear part (V2) with a circular cross-section perpendicular to said disk-shaped part (V1), and
   wherein said lid (U) is comprised of a circular element having an elongated hole or slot (U1) in a radial direction configured to put the seat or compartment (T2) of the translating assembly (T) in communication with an outer environment, through which the second part (V2) of the valve (V) is housed and protrudes, and one or more additional through holes (U2).

2. The pump to produce or improve human penis erection, according to claim 1, wherein said inner assembly (C) has raised reliefs or ribs on an outer surface arranged parallel to a length of the inner assembly, which are configured to facilitate a sliding of the translating assembly (T) over the inner assembly (C) and to facilitate an outflow of water present between the bellows (S) and the inner assembly (C).

3. The pump to produce or improve human penis erection, according to claim 1, wherein said lid (U) comprises one or more additional through holes (U2) configured to put the seat or compartment (T2) of the translating assembly (T) in communication with the outer environment.

4. The pump to produce or improve human penis erection, according to claim 1, wherein said lid (U) comprises, on an edge facing inside the translating assembly (T), one or more recesses or seats (U4) configured to facilitate application removal of said lid (U) from the translating assembly (T).

5. The pump to produce or improve human penis erection, according to claim 1, wherein said valve (V) comprises a third generally rectangular wall-shaped part (V3), joined to said first disc-shaped part (V1) on a same side as said second linear part (V2), in a space between an edge of said first disc-shaped part (V1) and said second linear part (V2), and wherein said lid (U) has on a side facing inside the translating assembly (T), a seat or compartment (U3) for housing said third wall-shaped part (V3) of the valve (V).

6. The pump to produce or improve human penis erection, according to claim 5, wherein said valve (V) comprises radial reliefs (V5) on a circumference of its first substantially disc-shaped part (V1).

7. The pump to produce or improve human penis erection, according to claim 5, wherein said valve (V) comprises an annular or circular gasket (V4) made of an elastic material on a side of said first disc-shaped part (V1) opposite to said second part (V2) and third part (V3).

8. The pump to produce or improve human penis erection, according to claim 1, further comprising an air-tight annular gasket (G) having an element made of a flexible material, applied on an edge (S1) of the bellows (S) corresponding to the rimmed annular edge (C1) of the inner assembly (C).

9. The pump to produce or improve human penis erection, according to claim 8, wherein a central hole (G2) of said annular gasket (G) and a corresponding hole of the bellows (S) are eccentric with respect to a circumferences of their outer edges (G1, S1).

* * * * *